(12) United States Patent
Cregger et al.

(10) Patent No.: US 10,823,715 B2
(45) Date of Patent: Nov. 3, 2020

(54) CHEMICAL INDICATOR FOR MONITORING HYDROGEN PEROXIDE STERILIZATION AND DISINFECTION PROCESSES

(71) Applicant: American Sterilizer Company, Mentor, OH (US)

(72) Inventors: Tricia Cregger, Fairlawn, OH (US); Phillip F. Franciskovich, Concord, OH (US)

(73) Assignee: American Sterilizer Company, Mentor, OH (US)

(*) Notice: Subject to any disclaimer, the term of this patent is extended or adjusted under 35 U.S.C. 154(b) by 371 days.

(21) Appl. No.: 15/653,560

(22) Filed: Jul. 19, 2017

(65) Prior Publication Data

US 2019/0025268 A1    Jan. 24, 2019

(51) Int. Cl.
| | |
|---|---|
| *G01N 31/22* | (2006.01) |
| *G01N 21/78* | (2006.01) |
| *A61L 2/28* | (2006.01) |
| *C12Q 1/22* | (2006.01) |

(52) U.S. Cl.
CPC ............... *G01N 31/228* (2013.01); *A61L 2/28* (2013.01); *C12Q 1/22* (2013.01); *G01N 21/78* (2013.01); *G01N 31/226* (2013.01); *G01N 31/229* (2013.01)

(58) Field of Classification Search
CPC ........... G01N 31/22; G01N 21/78; A61L 2/28
USPC ........................................................ 436/135
See application file for complete search history.

(56) References Cited

U.S. PATENT DOCUMENTS

| | | | |
|---|---|---|---|
| 2,606,654 A | | 8/1952 | Davis et al. |
| 2,880,072 A | * | 3/1959 | Grosskopf ............. G01N 31/22 |
| | | | 436/133 |
| 3,021,191 A | * | 2/1962 | Rhodes ..................... C09C 1/26 |
| | | | 423/367 |
| 3,096,189 A | * | 7/1963 | Kranz ...................... B41M 5/10 |
| | | | 106/236 |
| 3,238,020 A | * | 3/1966 | Eiseman, Jr. ........ G01N 31/221 |
| | | | 422/420 |

(Continued)

FOREIGN PATENT DOCUMENTS

| | | | |
|---|---|---|---|
| EP | 1217373 | | 6/2002 |
| JP | 52-74407 | * | 6/1977 |

(Continued)

OTHER PUBLICATIONS

Eisenberg, G. M., Industrial and Enginerring Chemistry 1943, 15, 327-328.*

(Continued)

*Primary Examiner* — Arlen Soderquist
(74) *Attorney, Agent, or Firm* — Renner, Otto, Boisselle & Sklar, LLP (57) ABSTRACT

This invention relates to a chemical indicator for monitoring a vaporous hydrogen peroxide sterilization process. The chemical indicator comprises a reactive composition adhered to a substrate, the reactive composition comprising a transition metal reagent, an oxidizing agent, and a resin. A test pack containing the chemical indicator and a biological indicator is disclosed. Vaporous hydrogen peroxide sterilization processes using the chemical indicator and the test pack are disclosed.

9 Claims, 4 Drawing Sheets

(56) References Cited

U.S. PATENT DOCUMENTS

| | | | |
|---|---|---|---|
| 3,664,883 A * | 5/1972 | Henry | G01N 21/91 148/241 |
| 3,896,039 A * | 7/1975 | Jacoby | C09K 3/22 252/88.1 |
| 4,098,120 A | 7/1978 | Manske | |
| 4,256,694 A * | 3/1981 | McAllister | G01N 31/224 422/416 |
| 4,291,122 A | 9/1981 | Orelski | |
| 4,323,477 A * | 4/1982 | Hill | A01N 59/20 106/15.05 |
| 4,421,719 A * | 12/1983 | Burleigh | G01N 30/95 422/416 |
| 4,461,837 A | 7/1984 | Karle et al. | |
| 4,521,375 A * | 6/1985 | Houlsby | A61L 12/124 422/29 |
| 4,885,253 A | 12/1989 | Kralovic | |
| 5,139,957 A * | 8/1992 | Grack | G01N 31/228 422/424 |
| 5,364,767 A * | 11/1994 | Flowers | C07D 209/36 435/14 |
| 5,405,580 A | 4/1995 | Palmer | |
| 5,439,827 A * | 8/1995 | Yagi | C12Q 1/26 422/420 |
| 5,496,739 A * | 3/1996 | Loescher | G01N 31/22 436/131 |
| 5,500,184 A | 3/1996 | Palmer | |
| 5,516,489 A * | 5/1996 | Melgaard | G01N 1/22 422/68.1 |
| 5,552,320 A | 9/1996 | Smith | |
| 5,620,579 A * | 4/1997 | Genshaw | C12Q 1/004 204/402 |
| 5,702,955 A * | 12/1997 | Pugia | G01N 31/228 436/135 |
| 5,736,355 A | 4/1998 | Dyke et al. | |
| 5,770,393 A | 6/1998 | Dalmasso et al. | |
| 5,801,010 A | 9/1998 | Falkowski et al. | |
| 5,834,626 A | 11/1998 | De Castro et al. | |
| 5,942,438 A | 8/1999 | Antonoplos et al. | |
| 5,955,025 A * | 9/1999 | Barrett | A61L 2/28 116/206 |
| 6,063,631 A * | 5/2000 | Ignacio | A61L 2/14 422/28 |
| 6,218,189 B1 | 4/2001 | Antonoplos et al. | |
| 6,355,448 B1 | 3/2002 | Foltz et al. | |
| 6,436,659 B1 | 8/2002 | Hui et al. | |
| 6,551,555 B2 | 4/2003 | Antonoplos et al. | |
| 6,790,411 B1 * | 9/2004 | Read | A61L 2/28 206/438 |
| 6,924,139 B2 | 8/2005 | Eveland et al. | |
| 7,045,343 B2 | 5/2006 | Witcher et al. | |
| 7,950,794 B2 | 5/2011 | Vanini | |
| 8,043,845 B2 | 10/2011 | Franciskovich et al. | |
| 8,802,392 B2 | 8/2014 | Chandrapati et al. | |
| 8,822,174 B1 | 9/2014 | Franciskovich et al. | |
| 8,840,837 B2 | 9/2014 | Smith et al. | |
| 8,969,029 B2 | 3/2015 | Chandrapati et al. | |
| 8,975,067 B2 | 3/2015 | Foltz et al. | |
| 8,980,622 B2 | 3/2015 | Smith et al. | |
| 9,017,994 B2 | 4/2015 | Franciskovich et al. | |
| 9,322,046 B2 | 4/2016 | Chandrapati et al. | |
| 9,540,677 B2 | 1/2017 | Smith et al. | |
| 9,671,378 B2 * | 6/2017 | Akbari Khorami | G01N 31/228 |
| 2002/0058296 A1 | 5/2002 | Miller et al. | |
| 2002/0121629 A1 * | 9/2002 | Mikumo | A61L 2/28 252/408.1 |
| 2003/0036202 A1 * | 2/2003 | Teodorcyzk | G01N 33/521 436/63 |
| 2003/0194346 A1 * | 10/2003 | Read | A61L 2/28 422/28 |
| 2004/0026244 A1 * | 2/2004 | Hodges | C12Q 1/004 204/409 |
| 2004/0248235 A1 | 12/2004 | Foltz et al. | |
| 2004/0265170 A1 * | 12/2004 | Read | A61L 2/28 422/403 |
| 2007/0054412 A1 * | 3/2007 | Cregger | C09B 21/00 436/166 |
| 2008/0267811 A1 * | 10/2008 | Yamaguchi | G01N 31/223 422/3 |
| 2009/0047176 A1 * | 2/2009 | Cregger | A61L 2/28 422/28 |
| 2009/0098662 A1 * | 4/2009 | Birch | G01N 33/54313 436/525 |
| 2009/0301382 A1 * | 12/2009 | Patel | G01D 3/10 116/201 |
| 2010/0143930 A1 * | 6/2010 | Cregger | C12Q 1/22 435/5 |
| 2010/0200432 A1 * | 8/2010 | Kamata | C12Q 1/006 205/792 |
| 2011/0012954 A1 | 1/2011 | Brown et al. | |
| 2011/0064610 A1 * | 3/2011 | Stammel | G01N 31/226 422/29 |
| 2011/0211991 A1 | 9/2011 | Foltz et al. | |
| 2012/0196355 A1 * | 8/2012 | Franciskovich | C12Q 1/22 435/287.4 |
| 2013/0089922 A1 | 4/2013 | Franciskovich et al. | |
| 2013/0217001 A1 * | 8/2013 | Franciskovich | G01N 21/6486 435/5 |
| 2013/0273594 A1 * | 10/2013 | Ahimou | A61L 2/28 435/31 |
| 2014/0013988 A1 * | 1/2014 | Newell | F42B 30/006 102/513 |
| 2014/0273072 A1 * | 9/2014 | Franciskovich | C12N 15/74 435/31 |
| 2014/0273073 A1 * | 9/2014 | Franciskovich | C12Q 1/22 435/31 |
| 2015/0004682 A1 | 1/2015 | Smith et al. | |
| 2015/0050745 A1 * | 2/2015 | Karato | G01N 31/226 436/135 |
| 2015/0147773 A1 * | 5/2015 | Franciskovich | A61L 2/28 435/31 |
| 2015/0159192 A1 | 6/2015 | Foltz et al. | |
| 2016/0131622 A1 * | 5/2016 | Akbari Khorami | G01N 31/228 436/135 |
| 2016/0186120 A1 | 6/2016 | Chandrapati et al. | |
| 2017/0252471 A1 | 9/2017 | Patel | |
| 2017/0269058 A1 * | 9/2017 | Denney | G01N 33/493 |
| 2017/0342277 A1 | 11/2017 | Sampathkumaran et al. | |
| 2018/0156765 A1 * | 6/2018 | Lobbert | G01N 21/78 |
| 2018/0269481 A1 * | 9/2018 | Motallebi | H01M 4/58 |

FOREIGN PATENT DOCUMENTS

| | | | |
|---|---|---|---|
| JP | 54-106308 | * | 8/1979 |
| WO | 98/46994 | * | 10/1998 |
| WO | 2007046865 A1 | | 4/2007 |
| WO | 2008082728 A2 | | 7/2008 |
| WO | 2009149243 A1 | | 12/2009 |

OTHER PUBLICATIONS

Bobtelsky, M. et al, Journal of the American Chemical Society 1945, 67, 966-975.*
Koncki, R. et al, Sensors and Actuators B 1998, 51, 355-358.*
Del Villar, I. et al, Sensors and Actuators B 2005, 108, 751-757.*
Khorami, H. A. et al, Electrochimica Acta 2014, 115, 416-421.*
Khorami, H. A. et al, International Journal of Health and Medical Engineering 2015, 9, 1210-2014.*
Pandey, P. C. et al, Electrochimica Acta 2016, 190, 758-765.*
Sun, J. et al, Sensors 2016, 16, paper 584, 11 pages.*
Koren, K. et al, Analyst 2016, 141, 4332-4339.*
Gasset, A. R. et al, Archives of Ophthalmology 1975, 93, 412-415.*
International Search Report and Written Opinion, Application No. PCT/US2018/036010, dated Jan. 14, 2019.
Pigment Dispersions & Formulations for Inkjet Inks: PenColor, Inc.; "Solutions in Plastic & Coatings Formulations"; www.pencolor.com/en/industries/inks-a-coatings/inkjet-inks; printed Aug. 26, 2016; 2 pages.

(56) References Cited

OTHER PUBLICATIONS

KolorJet Chemicals PVT.Ltd. Product Information; www.kolorjetchemicals.com/inkjet-dyes.html; printed Aug. 26, 2016; 4 pages.
Dow; Polypropylene Glycols and Copolymers North America; Polypropylene Glycols (PPGs); www.dow.com/polyglycols/ppgc/na/products/ppgs.htm ; printed Aug. 26, 2016; 1 page.
Lubrizol; Chemindustry; Polypropylene glycol 4000, CAS No. 25323-30-2; www.chemindustry.com/chemicals/0618168.htm; printed Aug. 26, 2016; 2 pages.

* cited by examiner

CHEMICAL INDICATOR FOR MONITORING HYDROGEN PEROXIDE STERILIZATION AND DISINFECTION PROCESSES

TECHNICAL FIELD

This invention relates to a chemical indicator for monitoring hydrogen peroxide sterilization and disinfection processes.

BACKGROUND

It is a common practice in the field of sterilization to have indicators present during the sterilization of articles, such as medical devices, to provide assurance that the sterilization process is effective.

SUMMARY

Chemical Indicators are used to detect semi-quantifiable to quantifiable amounts of an active ingredient in a sterilant used in a sterilization process. The use of a chemical indicator with a load provides assurance that the required amount of the active ingredient for effecting sterilization is used. The chemical indicator may be placed within a load to demonstrate that the sterilant successfully penetrated the processed load.

Chemical indicators for vaporous hydrogen peroxide (VHP) sterilization processes may rely on the oxidative nature of the hydrogen peroxide to provide a distinct color change for the chemical indicator. While prior art chemical indicators for monitoring VHP sterilization processes may be at least partly effective, a problem in the art relates to the fact that most of the color change occurs very rapidly within the sterilization cycle, and as a result the entire sterilization cycle is not monitored. This invention overcomes this problem by providing a chemical indicator that allows for a delayed change in color during the sterilization cycle. This allows for monitoring more of or all of the sterilization cycle.

This invention relates to a chemical indicator for monitoring a vaporous hydrogen peroxide (VHP) sterilization process, comprising: a reactive composition adhered to a substrate; the reactive composition comprising a transition metal reagent, an oxidizing agent selected from potassium dichromate, sodium dichromate, potassium permanganage, or a mixture of two or more thereof, and a resin for adhering the transition metal reagent and the oxidizing agent to the substrate.

This invention also relates to a test pack containing the chemical indicator as well as a biological indicator. This invention also relates to a VHP sterilization process for sterilizing a load using the chemical indicator to indicate whether the required amount of the active ingredient of the sterilant is used for the sterilization cycle.

BRIEF DESCRIPTION OF THE DRAWINGS

In the annexed drawings, like parts and features have like designations.

DETAILED DESCRIPTION

All ranges and ratio limits disclosed in the specification and claims may be combined in any manner. It is to be understood that unless specifically stated otherwise, references to "a," "an," and/or "the" may include one or more than one, and that reference to an item in the singular may also include the item in the plural.

The phrase "and/or" should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The word "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," may refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The transitional words or phrases, such as "comprising," "including," "carrying," "having," "containing," "involving," "holding," and the like, are to be understood to be open-ended, i.e., to mean including but not limited to.

The term "inactivation" of a test organism (e.g., bacterial spores) refers to the loss of ability of the test organism to germinate, outgrow and/or multiply.

The term "log reduction" is a mathematical term to show the number of live test organisms (e.g., bacterial spores) inactivated by contacting the test organisms with a sterilant. A "4 log reduction" means that the number of live test organisms is 10,000 times smaller. A "5 log reduction" means that the number of live test organisms is 100,000 times smaller. A "6 log reduction" means that the number of live test organisms is 1,000,000 times smaller.

The term "sterilization" is often taken to refer to a process wherein a total absence of living test organisms is achieved. However, this term is also used herein to refer to processes that are less rigorous than sterilization processes. These may include, for example, disinfection, sanitization, decontamination, cleaning, and the like. The sterilization processes provided for herein may be conducted for an effective period of time to achieve at least about a 4 log reduction, or at least about a 5 log reduction, or at least about a 6 log reduction in the number of test organisms capable of germination, outgrowth and/or multiplication.

The term "biological indicator" refers to a microbiological test system which comprises a test organism. The biological indicator may comprise a carrier and a plurality of the test organisms deposited on the carrier. The biological indicator may be used in combination with the inventive chemical indicator.

The term "carrier" refers to a supporting material onto which test organisms may be deposited.

The term "inoculated carrier" refers to a carrier onto which test organisms have been deposited.

The term "test organism" refers to a microorganism used in a sterilization process to monitor the process of the sterilization process. The test organism by design will be more resistant to the sterilization process than the organisms to be destroyed by the sterilization process. This is to insure that if the test organism is destroyed, any harmful organisms intended for destruction with the sterilization process will also be destroyed. The test organism may comprise a plurality of spores, for example, bacterial spores.

Figure 1:
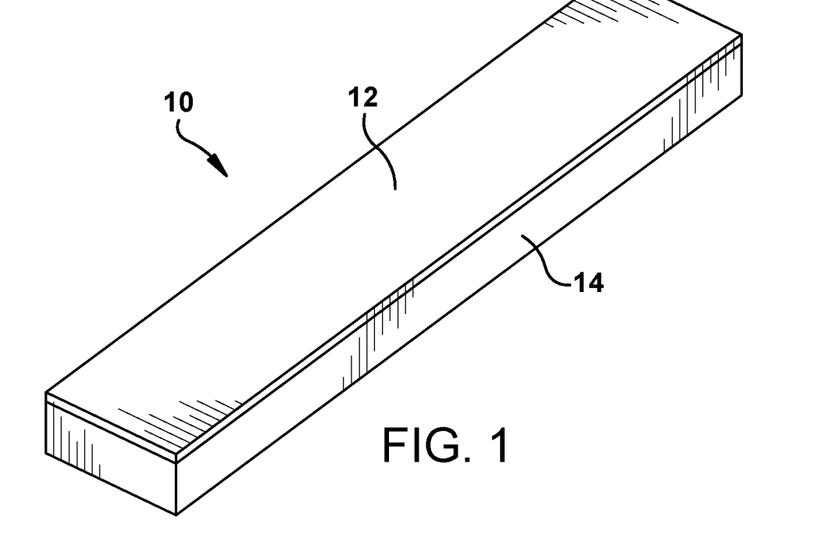
FIG. 1 is a schematic illustration of a chemical indicator within the scope of the invention.

The inventive chemical indicator is illustrated in FIG. 1 Referring to FIG. 1, chemical indicator 10 comprises reactive composition 12 adhered to substrate 14. The reactive composition 12 may comprise a transition metal reagent; an oxidizing agent selected from potassium dichromate, sodium dichromate, potassium permanganate, or a mixture of two or more thereof; and a resin. The resin is used as a binder to adhere the transition metal reagent and the oxidizing agent to the substrate.

While not wishing to be bound by theory, it is believed that in use in a sterilization process wherein the sterilant is vaporous hydrogen peroxide (VHP), the transition metal reagent reacts with part of the VHP contacting the chemical indicator 10. This results in part (for example, from about 10% to about 90%, or from about 30% to about 70%) of the VHP contacting the chemical indicator 10 being consumed. The oxidizing agent then reacts with the remainder of the VHP contacting the chemical indicator 10. This sequence of reactions results in a delayed color change for the chemical indicator 10.

The delayed color change provided by the inventive chemical indicator provides the advantage of allowing for more of the sterilization cycle to be monitored by the chemical indicator. As such, the inventive chemical indicator requires a longer exposure time to the VHP sterilant to turn color as compared to currently available chemical indicators. Thus, for example, the inventive chemical indicator may require 2 to 4, or 3 to 4 pulses of sterilant before it turns color, while currently available indicators may turn color after only 1 or 2 pulses of sterilant. The delay in color change provided by the inventive chemical indicator allows for the inventive chemical indicator to monitor more of or all of a VHP sterilization cycle, while the currently available indicators may only monitor the early stages, for example, the first quarter or first half of the sterilization cycle.

The transition metal reagent may comprise iron, copper, nickel, manganese, molybdenum, zinc, titanium, vanadium, silver, cobalt, platinum, or a combination of two or more thereof. The transition metal reagent may comprise iron. The transition metal reagent may comprise potassium ferricyanide, Prussian blue, Turnbull blue, potassium iron (III) hexacyanoferrate, sodium ferricyanide, or a mixture of two or more thereof.

The reactive composition 12 may include the transition metal reagent at a concentration (without water) in the range from about 20 to about 65% by weight, or from about 35 to about 50% by weight.

The reactive composition 12 may contain (without water) from about 0.01 to about 15% by weight of the oxidizing agent, or from about 0.25 to about 5% by weight.

The resin may comprise gum arabic; gum ghatti; guar gum; locust (carob)bean gum; karaya gum; gum tragacanth; chicle; rosin ester; tall oil; manila copais; corn gluten; coumarone-indene resin; crown gum; damar gum; polydimethylstyrene; gum elemi; rosin glycerol ester; ethylene vinyl acetate; polyamide; ethylene oxide polymer; ethylene oxide/propylene oxide copolymer; galbanum resin; gellan gum; ghatti gum; gluten gum; gualac gum; guarana gum; heptyl paraben; cellulose resin; isobutylene-isoprene copolymer; mastic gum; oat gum; opopanax gum; polyacrylamide; polylimonene; polyisobutylene; polymaleic acid; polypropylene glycol; polyvinyl acetate; polyvinyl alcohol; polyvinyl polypyrrolidone; rosin adduct with fumaric acid and pentaerythritol ester; rosin, gum, glycerol ester; rosin, gum or wood pentaerythritol ester; rosin, gum or wood, partially hydrogenated glycerol ester; rosin, gum or wood, partially hydrogenated, pentaerythritol ester; rosin, partially hydrogenated methyl ester; rosin, partially dimerized, glycerol ester; partially hydrogenated rosin; rosin, polymerized glycerol ester; rosin, tall oil glycerol ester; rosin, wood; rosin, wood, glycerol ester; shellac; polystyrene; styrene terpolymer; styrene copolymer; sucrose acetate isobutyrate; terpene resin; turpentine gum; polyvinylacetate; vinyl chloride-vinylidene chloride copolymer; zanthan gum; zein, or a mixture of two or more thereof. The resin may comprise polypropylene glycol, for example, polypropylene glycol with a molecular weight of about 4000. The concentration of the resin (without water) in the reactive composition may be in the range from about 25 to about 75% by weight, or from about 50 to about 65% by weight.

In an embodiment, the reactive composition may comprise from about 20 to about 65% by weight or about 35 to about 50% by weight potassium ferricyanide; from about 0.01 to about 15% by weight, or from about 0.25 to about 5% by weight potassium dichromate; and from about 25 to about 75% by weight, or from about 50 to about 65% by weight polypropylene glycol.

The substrate may comprise a porous substrate or a non-porous substrate. The substrate may comprise paper, polyester film, aluminum foil, or a combination of two or more thereof. The substrate may comprise paper laminated with a polymer film. The substrate may comprise mylar, metal foil, metallized foil, polyester, polyolefin, polycarbonate, polystyrene, polyacrylamide, polymethacrylate, poly(methyl)methacrylate, polyimide, polyethylene terephthalate, polybutylene terephthalate, polyvinylchloride, or a combination of two or more thereof.

The substrate may have any desired configuration, for example, a rectangle, square, circle, oval, and the like. The substrate may have a length (or diameter) in the range from about 0.5 to about 20 centimeters (cm), or from about 3 to about 10 cm; a width in the range from about 0.25 to about 10 cm, or from about 0.5 to about 2 cm; and a thickness in the range from about 0.25 to about 25 microns, or from about 0.5 to about 10 microns.

The chemical indicator may be made by a process comprising: (a) forming an aqueous composition comprising the transition metal reagent, oxidizing agent and water; (b) combining the aqueous composition from (a) with the resin to form a coatable composition; and (c) applying the coatable composition to the substrate. The composition may be allowed to dry to form a layer in the form of a dry film of the reactive composition on the substrate. The aqueous composition formed during step (a) may comprise: from about 5 to about 30% by weight, or from about 8 to about 20% by weight, of the transition metal reagent; from about 0.05 to about 5% by weight, or from about 0.1 to about 0.75% by weight, oxidizing agent; and from about 40 to about 80% by weight, or from about 55 to about 75% by weight, water. The weight ratio of the aqueous composition to the resin in (b) may be from about 8 to about 30, or from about 12 to about 25. The coatable composition may be sprayed, brushed, rolled or printed onto the substrate. The coatable composition may be ink jet printed onto the substrate.

The concentration of the reactive composition on the substrate (after drying) may be in the range from about 0.1 to about 1.8 grams per square centimeter, or from about 0.45 to about 1.4 grams per square centimeter. The chemical indicator may comprise one or more layers (for example, 2 to 5 layers, or 2 to 4 layers, or 2 to 3 layers or 2 layers) of the reactive composition on the substrate. The one or more layers of the reactive composition may have a dry film thickness in the range from about 0.5 to about 150 microns, or from about 3 to about 50 microns.

Figure 2:
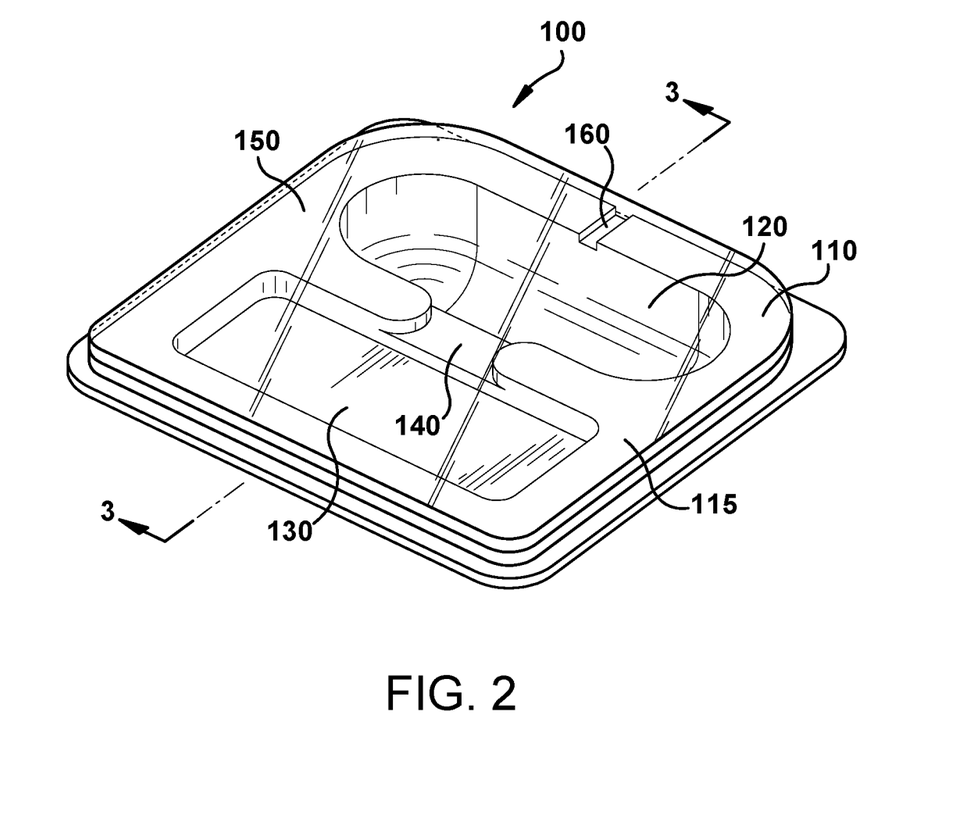
FIG. 2 is a schematic illustration of a test pack that can be used with the chemical indicator of FIG. 1.
Figure 3:
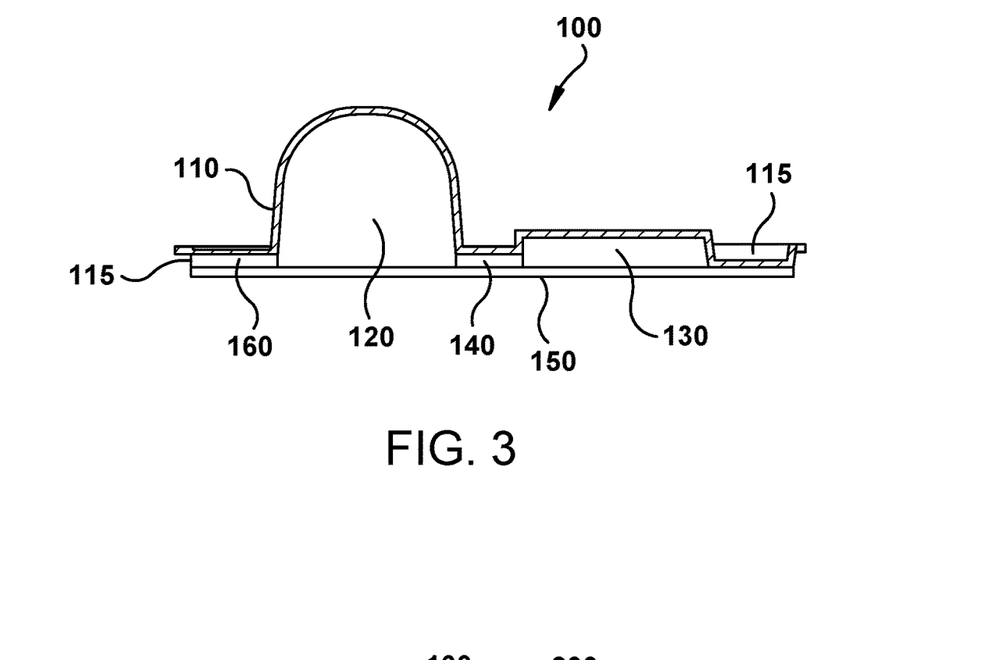
FIG. 3 is a cross-sectional view of the test pack illustrated in FIG. 2 taken along line 3-3 of FIG. 2.
Figure 4:
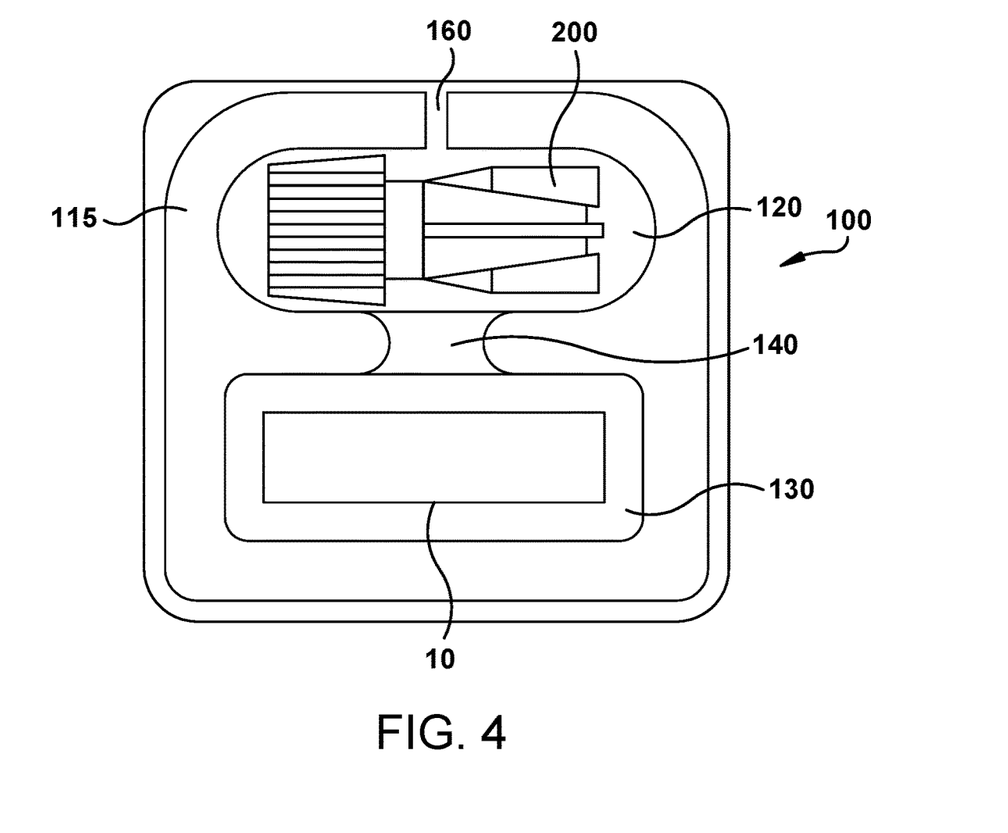
FIG. 4 is a top plan view of the test pack of FIG. 2 with a self-contained biological indicator (SCBI) in a first containment section of the test pack and a chemical indicator in a second containment section of the test pack.
Figure 5:
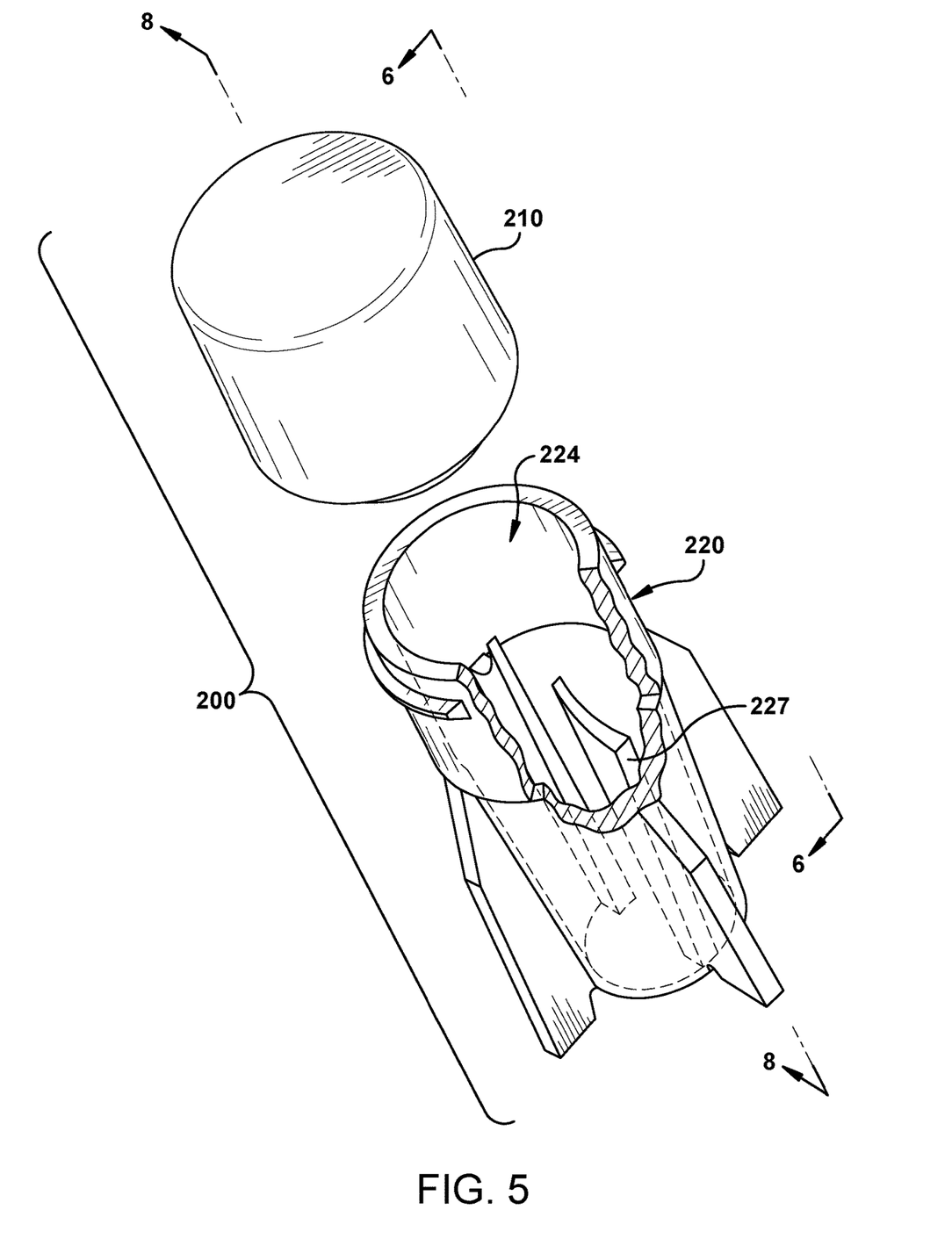
FIG. 5 is a perspective view of an SCBI which can be used in the test pack illustrated in FIGS. 2-4.

The chemical indicator 10 may be used with the test pack 100 depicted in FIGS. 2-4. Referring to FIGS. 2-4, test pack 100 includes base 110 containing first containment section 120, second containment section 130, and peripheral surface 115 which surrounds containment sections 120 and 130. The containment sections 120 and 130 are configured to allow for the flow of sterilant from one to the other via internal channel 140. Cover 150 is attached to the base 110 and forms a sealed enclosure for the containment sections 120 and 130, and internal channel 140. External channel 160 is formed in peripheral surface 115 into containment section 120. A self-contained biological indicator (SCBI) 200 is positioned in the first containment section 120. The chemical indicator 10 is positioned in the second containment section 130. The external channel 160 is configured to allow for the flow of sterilant from the external environment into the first containment section 120. The base 110 and cover 150 are otherwise impenetrable by the sterilant. The sterilant flows through external channel 160 into the first compartment section 120 and in contact with the SCBI 200, and also through the internal channel 140 into the second containment section 130 in contact with the chemical indicator 10. The chemical indicator 10 undergoes a change in color after it has been exposed to a desired quantity of sterilant. The degree of color change is indicative of the load intended for sterilization being contacted by a sufficient amount of sterilant to effect the desired level of sterilization.

The SCBI 200 may be in the form illustrated in FIGS. 5-8. Referring to FIGS. 5-8, SCBI 200 includes cap 210 which is configured for housing fluid 240. The fluid 240 contains a growth media. Cap 210, which is mounted on container 220, includes inner chamber 216. The inner chamber 216 has an opening 215 with a breakable barrier 230 covering the opening 215. The fluid 240 is encapsulated within the inner chamber 216. The container 220 has an interior region 224 where inoculated carrier 290 is positioned.

The inoculated carrier 290 may be formed by inoculating a carrier 290 with an aqueous composition containing test organisms. The test organisms may comprise spores, for example, bacterial spores. The test organism may comprise spores of the Bacillus or Clostridia genera. The test organism may comprise spores of Geobacillus stearothermophilus, Bacillus atrophaeus, Bacillus sphaericus, Bacillus anthracis, Bacillus pumilus, Bacillus coagulans, Clostridium sporogenes, Clostridium difficile, Clostridium botulinum, Bacillus subtilis globigii, Bacillus cereus, Bacillus circulans, or a mixture of two or more thereof. The test organism may comprise spores of Geobacillus stearothermophilus. The concentration of the test organisms in the aqueous composition may range from about $10^4$ to about $10^8$ colony forming units (cfu) per milliliter (ml), or from about $10^5$ to about $10^7$ cfu/ml.

The carrier 290 may comprise a porous material or a non-porous material. The carrier may comprise a solid material. The carrier may comprise any material that does not dissolve or deteriorate during the sterilization or incubation processes. The carrier 290 may comprise an interior surface of container 220. The carrier may comprise paper, metal, glass, ceramics, plastic, membranes, or a combination of two or more thereof. The metal may comprise aluminum or steel. The plastic may comprise a polyolefin, polystyrene, polycarbonate, polymethacrylate, polyacrylamide, polyimide, polyester, and the like. The carrier may comprise a film. The carrier may be in the form of a spun or unwoven felt. The carrier may comprise a mat of compressed fibers. The carrier may comprise a porous material made of sintered glass, glass fibers, ceramic, synthetic polymer, or a combination of two or more thereof. The carrier may comprise filter paper or absorbent paper. The carrier may comprise a cellulose pad.

The aqueous composition used to inoculate the carrier 290 may contain a desired number of test organisms per aliquot for inoculating the carrier. The test organisms may be dispensed and allowed to dry on the carrier. An air flow may be used to dry the test organisms on the carrier, such as, for example, by placing the carrier in a laminar flow-hood to hasten the drying process. The method of drying the test organisms on the carrier may include allowing the test organisms to air dry by leaving them stand under ambient conditions, placing the inoculated test organisms in a desiccator containing a desiccant such as calcium chloride, in a temperature and humidity controlled environmental chamber, or placing the inoculated carrier under a stream of dry air, nitrogen or other anhydrous gas. The number of colony forming units of the test organism supported by the carrier may be in the range from about $10^4$ to about $10^7$ cfu per square millimeter of support (cfu/mm$^2$), or from about $10^5$ to about $10^6$ cfu/mm$^2$.

The chemical indicator 10, along with the test pack 100 and SCBI 200, may be used with any VHP sterilization process. The test pack 100 along with the load to be sterilized may be placed in a sterilization chamber and exposed to the sterilant during the sterilization process. The test pack 100 may be placed in the sterilization chamber in one or more locations where it is difficult for sterilant to reach to verify that the sterilant is penetrating these locations. Upon completion of the sterilization process, the test pack 100 may be removed from the sterilization chamber. The chemical indicator 10 may be checked for color change. The test organisms in the SCBI 200 may be incubated in the presence of a growth media to determine whether the sterilization process is effective.

Figure 6:
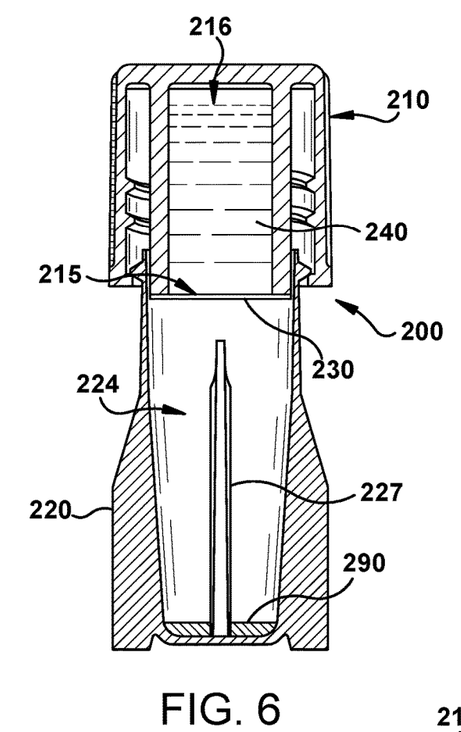
FIG. 6 is a cross-sectional view of the SCBI of FIG. 5 taken along line 6-6 in FIG. 5, showing a cap mounted on a container in a first non-activated position.

When used in a sterilization process, the cap 210 is held in an open position as illustrated in FIG. 6. The SCBI 200 and the load to be sterilized (e.g., a medial device) are then subjected to a sterilization process. During the sterilization process, sterilant passes through openings between the cap 210 and the container 220 and flows into the interior region 220 where it contacts and acts upon the test organisms inoculated on the carrier 290.

Figure 7:
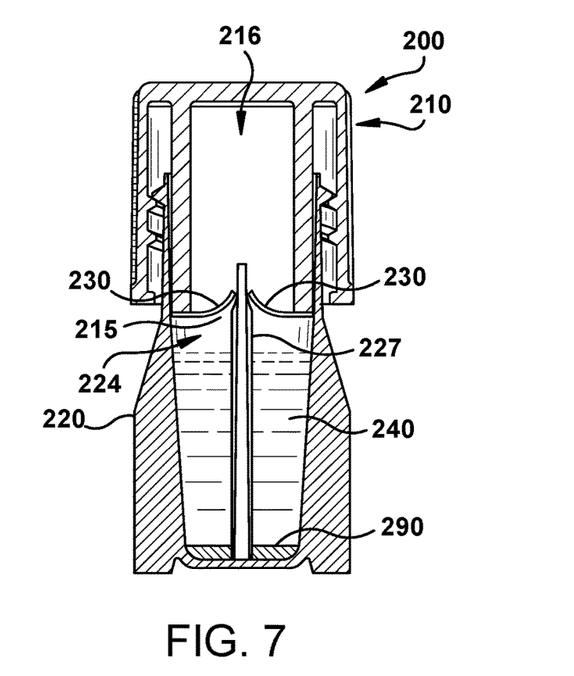
FIG. 7 is a cross-sectional view of the SCBI of FIG. 5 taken along line 6-6 in FIG. 5 showing the cap mounted on the container in a second activated position.
Figure 8:
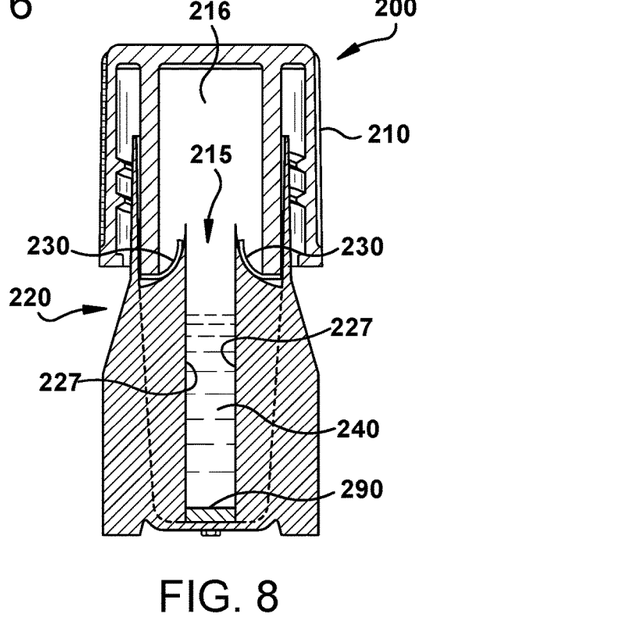
FIG. 8 is a cross-sectional view of the SCBI of FIG. 5 taken along line 8-8 in FIG. 5 showing the SCBI in a second activated position.

After the sterilization process is complete, the SCBI 200 is activated by screwing the cap 210 downward into a closed position as shown in FIGS. 7 and 8. This results in the breakable barrier 215 being broken by puncture member 227 to form broken barrier 230. (Note that two puncture members 230 may be used as shown in the embodiment depicted in FIG. 8). Fluid 240, which contains a growth media, then flows into the container 220 in contact with the test organisms deposited on the carrier 290.

While in container 220, the test organisms and growth media may be incubated for a sufficient period of time to determine the viability of the test organisms. At the end of the incubation period, the SCBI 200 is evaluated to determine whether any test organisms survive the sterilization process. If the test organisms survive the sterilization process, the sterilization process is not considered to have been successful. On the other hand, if the test organisms are inactivated, then the sterilization process is considered to be successful.

A more detailed description of the SCBI 200 is disclosed in U.S. Pat. No. 8,173,388, which is incorporated herein by reference. It should be noted that SCBI configurations other than those depicted in FIGS. 5-8 may be used.

The test pack 100 containing the chemical indicator 10 an the SCBI 200 may be used to release loads or validate sterilization chamber functionality in healthcare settings. The test pack 100 containing the chemical indicator 10 and the SCBI 200 may also be used to determine if biological indicator waste has been properly decontaminated. In the scientific setting, the test pack 100 containing the chemical indicator 10 and the SCBI 200 may be used to validate the functionality of sterilization chambers, release loads of goods, or validate that a process meets required functionality.

Following sterilization, a growth media may be brought into contact with the test organisms to provide for incubation. The growth media may be in the form of a liquid. The growth media may comprise a buffered aqueous solution. Any procedure whereby the test organisms are brought into contact with the growth media under conditions which allow for growth of the test organisms, if it still exists, may be used.

The growth media may comprise one or more nutrient sources. The nutrient source may be used to provide energy for the growth of any of the test organisms that may survive the sterilization process. Examples of the nutrient sources may include pancreatic digest of casein, enzymatic digest of soybean meal, sucrose, dextrose, yeast extract, L-cystine, and mixtures of two or more thereof.

A microbial growth indicator, which changes color or native state, in the presence of viable test organisms may be used with the growth media. The growth indicator may be dispersed or solubilized in the growth media and impart an initial color to the growth media. The growth indicator may also impart a color change in the growth media upon test organism growth. Growth indicators which may be employed include pH-sensitive dye indicators (such as bromothymol blue, bromocresol purple, phenol red, etc. or combinations thereof), oxidation-reduction dye indicators (such as methylene blue, etc.). The use of these microbial growth indicators may result in a change in color in response to a phenomenon of microorganism growth, such as changes in pH, oxidation-reduction potentials, enzymatic activity, as well as other indications of growth.

The growth media may further comprise one or more pH buffers, one or more neutralizers, one or more agents for maintaining osmotic equilibrium, or a mixture of two or more thereof. The pH buffers may include $K_2HPO_4$, $KH_2PO_4$, $(NH_4)_2HPO_4$, 2,2-Bis(hydroxylmethyl)-2,2',2"-nitrilothiethanol (Bis Tris), 1,3-Bis[tris(hydroxymethyl)methylamino] propane (Bis-Tris Propane), 4-(2-Hydroxyethyl)piperazine-ethanesulfonic acid (HEPES), 2-Amino-2-(hydroxymethyl)-1,3-propanediol (Trizma, Tris base), N-[Tris(hydroxymethyl)methyl]glycine (Tricine), Diglycine (Gly-Gly), N,N-Bis(2-hydroxyethyl)glycine (Bicine), N-(2-Acetamido)iminodiacetic acid (ADA), N-(2-Acetamido)-2-aminoethanesulfonic acid (aces), 1,4-Piperazinediethanesulfonic acid (PIPES), □-Hydroxy-4-morpholinepropanesulfonic acid (MOPSO), N,N-Bis(2-hydroxyethyl)-2-aminoethanesulfonic acid (BES), 3-(N-Morpholino)propanesulfonic acid (MOPS), 2-[(2-Hydroxy-1,1-bis(hydroxylmethyl)ethyl)amino]ethanesulfonic acid (TES), 3-(N,N-Bis[2-hydroxyethyl]amino)-2-hydroxypropanesulfonic acid (DIPSO), 4-(N-Morpholino)butanesulfonic acid (MOBS), 2-Hydroxy-3-[tris(hydroxymethyl)methylamino]-1-propanesulfonic acid (TAPSO), 4-(2-Hydroxyethyl)piperazine-1-(2-hydroxypropanesulfonic acid hydrate (HEPPSO), Piperazine-1,4-bis(2-hydroxypropanesulfonic acid) dihydrate (POPSO), 4-(2-Hydroxyethyl)-1-piperazine propanesulfonic acid (EPPS), N-(2-Hydroxyethyl)piperazine-N'-(4-butanesulfonic acid) (HEPBS), [(2-Hydroxy-1,1-bis(hydroxymethyl)ethyl)amino]-1-propanesulfonic acid (TAPS), 2-Amino-2-methyl-1,3-propanediol (AMPD), N-tris(Hydroxymethyl)methyl-4-aminobutanesulfonic acid (TABS), N-(1,1-Dimethyl-2-hydroxyethyl)-3-amino-2-hydroxypropanesulfonic acid (AMPSO), 2-(Cyclohexylamino)ethanesulfonic acid (CHES), 3-(Cyclohexylamino)-2-hydroxyl-1-propanesulfonic acid (CAPSO), 2-Amino-2-methyl-1-propanol (AMP), 3-(Cyclohexylamino)-1-propanesulfonic acid (CAPS), 4-(Cyclohexylamino)-1-butanesulfonic acid (CABS), 2-(N-Morpholino)ethanesulfonic acid hydrate (MES), N-(2-Acetamido)-2-aminoethanesulfonic acid (ACES), and mixtures of two or more thereof.

The neutralizers may include but are not limited to sodium thioglycollate, sodium thiosulfate, catalase, sodium bisulfate, sodium bisulfite lecithin, polysorbate 20, polysorbate 80, calcium bicarbonate, and mixtures of two or more thereof.

The agents for maintaining osmotic equilibrium may include sodium salt, potassium salts, magnesium salts, manganese salts, calcium salts, metallic salts, sodium chloride, potassium chloride, magnesium sulfate, iron chloride, and mixtures of two or more thereof.

The growth media may comprise an aqueous composition comprising: water; from about 0.01 to about 100 grams per liter (g/l or from about 0.1 to about 50 g/l, of one or more nutrient sources; from about $1.0 \times 10^{-5}$ to about 10 g/l, or from about $1.0 \times 10^{-4}$ to about 1.0 g/l of one or more microbial growth indicators; up to about 5000 g/l, or from about 0.001 to about 5000 g/l, or from about 0.1 to about 1000 g/l, of one or more pH buffers; up to about 100 g/l, or from about 0.01 to about 100 g/l, or from about 0.1 to about 50 g/l, of one or more neutralizers; up to about 50 g/l, or from about 0.1 to about 50 g/l, or from about 0.1 to about 25 g/l, of one or more agents for maintaining osmotic equilibrium.

EXAMPLE

A chemical indicator within the scope of the invention (the inventive chemical indicator) is prepared using Compositions 1 and 2.
Composition 1
  25.8 mg potassium dichromate
  1.0005 g potassium ferricyanide
  5 mls deionized (DI) water
Composition 2
  0.5388 g polypropylene glycol (molecular weight=4000).

Two milliliters (ml) of Composition 1 are added to Composition 2. The formulation is mixed and 1 ml of the mixed composition is transferred into an inkjet cartridge. A program that produces 48 rectangles (6 rows by 8 columns) is utilized and 4 layers are printed. The sample is cut into columns each containing 6 rectangles. The printed squares are yellow to yellowish orange in color.

A single strip of rectangles (the inventive chemical indicator) is placed into a sterilization pouch (compatible with VHP) along with a commercially available prior art chemical indicator. Samples are exposed to various lengths of a non-lumen sterilization cycle using VHP as the sterilant, some in fully loaded chambers and some in empty chambers. All cycles are run with a 2.1 g injection rate. The results are shown in Table 1. The inventive chemical indicator requires a longer exposure time to reach an end point color (dark green) than the prior art chemical indicator. The inventive chemical indicator requires 2 to 4 pulses of sterilant to change color as compared to the 1 to 2 pulses for the prior art chemical indicator. As such, the inventive chemical indicator monitors more of the sterilization cycle as compared to the prior art indicator.

TABLE 1

| Cycle Condition | Prior Art Indicator Color/Pass or Fail | Inventive Indicator Color/Pass or Fail |
| --- | --- | --- |
| Unexposed | Magenta/Fail | Yellow/Fail |
| 1 pulse full chamber (¼ cycle) | Magenta/Fail | Yellow/Fail |
| 2 pulses full chamber (½ cycle) | Yellow/Pass | Yellowish Green/Fail |
| 4 pulses full chamber (full cycle) | Yellow/Pass | Green/Pass |

The above-indicated formulation for the inventive chemical indicator is used to evaluate color change as a function of the number of layers used to make each rectangle following exposure to VHP. Samples comprising 2 and 4 printed layers are tested. Strips of rectangles are then exposed to various conditions of a sterilization cycle alongside a commercial prior art product. Table 2 shows the results. Changing the number of layers of reactive composition that are printed has an effect on when the indicator reaches its final color. As shown in Table 2, the change in the number of printed layers from 4 to 2 increases the exposure required to obtain a complete color change of the chemical indicator.

TABLE 2

| Cycle Condition | Prior Art Indicator Color/Pass or Fail | Inventive Indicator Color/Pass or Fail | |
| --- | --- | --- | --- |
| | | 4 layers | 2 layers |
| Unexposed | Magenta/Fail | Yellow/Fail | Yellow/Fail |
| 1 pulse full chamber (¼ cycle) | Yellow-Magenta/Fail | Yellow/Fail | Yellow/Fail |
| 2 pulses full chamber (½ cycle) | Magenta/Fail | Yellow-Green/Fail | Yellow-Green/Fail |
| 3 pulses full chamber (¾ cycle) | Yellow/Pass | Green/Pass | Green-Yellow/Fail |
| 4 pulses full chamber (full cycle) | Yellow/Pass | Green/Pass | Green/Pass |

With the present invention the chemical indicator takes longer to reach its complete color change. This lengthening of the time required to complete the color change means that the chemical indicator is monitoring more of the sterilization cycle than prior art chemical indicators. Additionally, the use of ink jet printing enables the manufacturer to easily control the amount of the reactive composition that is laid down on the chemical indicator substrate and tailor that amount for the various cycles and conditions that a sterilizer may require.

While the invention has been explained in relation to various embodiments, it is to be understood that various modifications thereof will become apparent to those skilled in the art upon reading the specification. Therefore, it is to be understood that the invention disclosed herein includes any such modifications that may fall within the scope of the appended claims.

What is claimed is:

1. A chemical indicator for monitoring a vaporous hydrogen peroxide sterilization process, comprising:
  a reactive composition adhered to a substrate, wherein the substrate is a non-porous substrate, the reactive composition being in the form of a dry film with a dry film thickness in the range from about 0.5 to about 150 microns, the concentration of the reactive composition on the substrate being in the range from about 0.1 to about 1.8 grams per square centimeter;
  the reactive composition comprising: from about 20% to about 65% by weight of a transition metal reagent, wherein the transition metal reagent is potassium ferricyanide, from about 0.01 to about 15% by weight of an oxidizing agent selected from potassium dichromate, and from about 25% to about 75% by weight of a resin for adhering the transition metal reagent and the oxidizing agent to the substrate, wherein the resin comprises polypropylene glycol.

2. The chemical indicator of claim 1 wherein the substrate comprises mylar, metal foil, metallized foil, polyester, polyolefin, polycarbonate, polystyrene, polyacrylamide, polymethacrylate, poly(methyl)methacrylate, polyimide, polyethylene terephthalate, polybutylene terephthalate, polyvinylchloride, or a combination of two or more thereof.

3. The chemical indicator of claim 1 wherein the substrate comprises polyester film, aluminum foil, or a combination thereof.

4. The chemical indicator of claim 1 wherein the substrate comprises paper laminated with a polymer film.

5. A process for making the chemical indicator of claim 1, comprising:
   (a) forming an aqueous composition comprising the transition metal reagent, the oxidizing agent and water;
   (b) combining the aqueous composition from (a) with the resin to form a coatable composition; and
   (c) applying the coatable composition to the substrate.

6. The process of claim 5 wherein the coatable composition is sprayed, brushed, rolled or printed onto the substrate.

7. The process of claim 5 wherein the coatable composition is ink jet printed onto the substrate.

8. A sterilization process, comprising:
   exposing an article to be sterilized and the chemical indicator of claim 1 to vaporous hydrogen peroxide.

9. A sterilization process, comprising:
   exposing an article to be sterilized and the chemical indicator of claim 1 to a sterilant comprising vaporous hydrogen peroxide; and
   determining whether a desired amount of sterilant contacts the article to be sterilized by observing color change in the chemical indicator.

* * * * *